(12) United States Patent
May et al.

(10) Patent No.: US 8,221,596 B2
(45) Date of Patent: Jul. 17, 2012

(54) HIGH IMPEDANCE SYSTEM FOR GENERATING ELECTRIC FIELDS

(75) Inventors: Wayne A. May, Las Vegas, NV (US); Peter Ruben, Calgary (CA)

(73) Assignee: May-Ruben Technologies, Inc., Calgary, Alberta (CA)

( * ) Notice: Subject to any disclaimer, the term of this patent is extended or adjusted under 35 U.S.C. 154(b) by 9 days.

(21) Appl. No.: 12/769,872

(22) Filed: Apr. 29, 2010

(65) Prior Publication Data
US 2011/0139608 A1  Jun. 16, 2011

Related U.S. Application Data

(62) Division of application No. 11/551,584, filed on Oct. 20, 2006.

(60) Provisional application No. 60/732,888, filed on Nov. 2, 2005.

(51) Int. Cl.
*C25B 9/00* (2006.01)
*C02F 1/46* (2006.01)

(52) U.S. Cl. ............ 204/230.2; 204/242; 204/663; 204/671; 204/672; 204/673

(58) Field of Classification Search ............ 204/230.2, 204/242, 663, 670–674
See application file for complete search history.

(56) References Cited

U.S. PATENT DOCUMENTS

| | | | |
|---|---|---|---|
| 2,919,235 A | 12/1959 | Roller | |
| 4,886,593 A | 12/1989 | Gibbs | |
| 5,134,070 A | 7/1992 | Casnig | |
| 5,234,555 A | 8/1993 | Ibbott | |
| 5,690,978 A | 11/1997 | Yin et al. | |
| 5,983,131 A | 11/1999 | Weaver et al. | |
| 6,090,617 A * | 7/2000 | Meserol | 435/285.2 |
| 6,455,014 B1 | 9/2002 | Hammerstrom et al. | |
| 6,562,386 B2 | 5/2003 | Ruan et al. | |

(Continued)

FOREIGN PATENT DOCUMENTS
JP   2004-202086 A   7/2004
(Continued)

OTHER PUBLICATIONS

Birmingham, J.G., (abstract) Mechanisms of Bacterial Spore Deactiviation Using Ambient Pressure Nonthermal Discharges, Plasma Science, Aug. 2004, pp. 1526-1531, vol. 32, Iss 4.

(Continued)

*Primary Examiner* — Arun S Phasge
(74) *Attorney, Agent, or Firm* — Greenberg Traurig (57) ABSTRACT

Disclosed is a system and method for generating time variant and invariant electric fields (E-fields) for various applications. Generating the E-field utilizes high impedance dielectric materials having a collection of three imperative material properties: high permittivity ($\in$), high volume resistivity ($\rho$) and high maximum allowable E-field stress ($\phi$) and physical geometries that take advantage of the manner in which E-fields are divided or distributed in series capacitance networks. The generated E-field can act upon a subject material, including a gas, liquid or solid, wherein the material is stationary or in motion. The method allows an E-field of given intensity to be set up in the subject material with a significantly lower applied voltage $\Phi_a$, or conversely, a significantly higher E-field intensity with a given applied voltage $\Phi_a$. The method forestalls electric conduction current through the subject material, thus significantly reducing electric conduction current, energy consumption, ohmic heating, and preempting electrochemical reactions at the electrode/fluid interfaces. Acoustic energy may also be applied.

24 Claims, 7 Drawing Sheets

U.S. PATENT DOCUMENTS

| | | |
|---|---|---|
| 6,617,154 B1 | 9/2003 | Meserol |
| 6,689,380 B1 | 2/2004 | Marchitto et al. |
| 6,692,456 B1 | 2/2004 | Eppstein et al. |
| 6,868,289 B2 | 3/2005 | Palti |
| 6,911,225 B2 | 6/2005 | Ruan et al. |
| 7,011,790 B2 | 3/2006 | Ruan et al. |
| 7,037,468 B2 | 5/2006 | Hammerstrom et al. |
| 2003/0132100 A1 | 7/2003 | Crowe et al. |
| 2008/0213855 A1 | 9/2008 | Firth et al. |

FOREIGN PATENT DOCUMENTS

| | | |
|---|---|---|
| JP | 2004-248653 A | 9/2004 |
| JP | 2004-532654 | 10/2004 |
| JP | 2005-526579 | 9/2005 |
| WO | WO 01/89455 | 11/2001 |
| WO | WO/03/063914 | 8/2003 |
| WO | WO 03/099382 | 12/2003 |
| WO | WO 2007-021994 A2 | 2/2007 |

OTHER PUBLICATIONS

Montenegro, et al, (abstract) Development of a Pulsed Non-thermal Plasma System for Microorganism Inactivation, Monograph Title-2000 ASAE Annual International Meeting, Milwaukee, Wisconsin, Jul. 9-12, 2000.

Lee, Sang-Wook; "A Micro Cell Lysis Device", Apr. 16, 1998; pp. 74-79; Sensors and Actuators 73 (1999); Pasadena, CA.

* cited by examiner

WHERE:
- -P AND +P — THE SILVER CONDUCTIVE ELECTRODE PLATES;
- $C_i$ — CAPACITIVE ELEMENT, DIELECTRIC INSULATING SLABS (CERAMIC);
- $C_d$ — CAPACITIVE ELEMENT, ELECTROLYTIC DOUBLE LAYER;
- $C_s$ — CAPACITIVE ELEMENT, SUPERNATANT LIQUID UNDER TREATMENT;
- $C_b$ — CAPACITIVE PARALLEL CONTRIBUTION, SUSPENDED BACTERIA FRACTION (LUMPED);
- $-C_m$ — MAXWELL-WAGNER INTERFACIAL CAPACITANCE ELEMENT, CELL MEMBRANE ON- SIDE;
- $+C_m$ — MAXWELL-WAGNER INTERFACIAL CAPACITIVE ELEMENT, ON + SIDE;
- $R_i$ — RESISTIVE ELEMENT, DIELECTRIC INSULATING SLABS (CERAMIC);
- $R_d$ — RESISTIVE ELEMENT, ELECTROLYTIC DOUBLE LAYER;
- $R_s$ — RESISTIVE ELEMENT, SUPERNATANT SUSPENSION LIQUID;
- $R_b$ — RESISTIVE PARALLEL CONTRIBUTION, SUSPENDED BACTERIA FRACTION (LUMPED);
- $-R_m$ — CELL MEMBRANE RESISTIVE ELEMENT ON THE - SIDE OF THE BACTERIA (LUMPED);
- $+R_m$ — CELL MEMBRANE RESISTIVE ELEMENT ON THE + SIDE OF THE BACTERIA (LUMPED);
- $R_c$ — CYTOPLASMIC RESISTIVE ELEMENT.

HIGH IMPEDANCE SYSTEM FOR GENERATING ELECTRIC FIELDS

CROSS-REFERENCE TO RELATED APPLICATIONS

This application is a divisional of U.S. application Ser. No. 11/551,584 filed Oct. 20, 2006, which claims the benefit of U.S. Provisional Application No. 60/732,888 filed Nov. 2, 2005.

FIELD OF THE INVENTION

The embodiments of the present invention relate to a system for applying time variant, time invariant, or pulsed voltage potential to a series capacitive network to set up or otherwise generate uniform or non-uniform electric fields, which in turn, are used for numerous applications. More particularly, the embodiments employ dielectric materials with particular electrical properties, arranged or otherwise configured to form series capacitance networks that divide or otherwise distribute the applied potential between opposing electrodes, resulting in a concentration of the E-field in (or otherwise through) a subject material.

BACKGROUND

Static, time variant, and pulsed electric fields, with or without a magnetic field component, whether considered weak or intense for a particular application, are used in a variety of industries for a broad range of applications. In some existing applications, and where time variant applied voltages are used with the embodiments of the present invention, charge carriers may be moving relative to the lab frame so a magnetic B-field component accompanies the electric E-field, however, with the embodiments of the present invention, only the E-field is pertinent. Examples of E-field applications include, but are not limited to the following:

- electrophoresis: both gel and capillary type employ an electrical current through suspension media, the resistive load, thus setting up an electric field used to separate, differentiate and fractionate DNA, proteins, and other molecules;
- electroporation (aka electropermeabilization): intense electric fields, often pulsed with various waveforms and pulse rates, are used to cause the dielectric breakdown of living cellular membranes, thus affecting reversible and nonreversible poration and/or permeabilization for the purpose of transfection, pasteurization or sterilization; and
- electric field flow fractionation (FFF, aka EFFF, μ-EFF, CyEFF, and others): employ an electric field orthogonal to a fluid flow in order to separate, fractionate, and differentiate large molecules and/or small particles from a subject liquid.

Generally speaking, a process or effect driven, supported or facilitated by the action of an E-field can be accelerated or otherwise improved by either increasing the field intensity for a given applied voltage, or conversely, by reducing the applied voltage for a given field intensity. This is due to the relationship between the material properties of permittivity, volume resistivity, and maximum allowable field stress, and the effect these parameters have on the diacritical circuit elements of field intensity, dielectric breakdown, field geometry, current flow, and energy consumption. Applications proceeding under the influence or direct action of an E-field are often limited by the undesirable effects of ohmic heating, electrochemistry (faradaic charge transfer), field shielding by electrolytic double layer formation, electrode polarization, and energy consumption.

Electric current is a limiting factor for the applied filed intensity in electrophoretic, electroporation, and field flow fractionation devices due to ohmic heating of the working media (usually a liquid or gel for such applications), and undesirable electrochemistry at the media/electrode interface(s) (faradaic charge transfer). For example, much effort has been expended over the last two decades to apply the process of clinical electroporation (primarily used for transfection of living biological cells) to commercial isothermal pasteurization (commonly know as Pulsed Electric Field non-thermal pasteurization or PEF). Reversible electroporation is non-lethal and is accomplished by careful control of the applied field intensity and exposure time, where irreversible electroporation is marked by cellular death, metabolic inactivation, or apoptosis. Due to the low impedance nature of PEF systems, where bare conductive electrodes are coupled directly to the fluid under treatment, pulsed voltage waveforms have been employed as a means to reduce average energy, ohmic heating, and undesirable electrochemistry at the fluid/electrode interface. The same is true for electrophoresis and electric field flow fractionation (EFFF) methods and devices. Although an increase in field intensity would improve the efficiency and/or rate of process, increasing the applied voltage as a means to increase field intensity results in excessive electric current and the associated ohmic heating, undesirable electrochemical reactions, and the other undesirable reactions referenced above. In the case of EFFF, recent efforts have been made to reduce the fluid channel height using micromachining and microelectronic techniques thereby effectively reducing the field dimension between the electrodes and thus increasing field intensity while mitigating electric current flow. Since increasing the E-field intensity also requires an increase in the applied voltage, and/or a decrease in the distance between the electrodes, dielectric breakdown of the working media, whether a gas, liquid, or solid, is an additional limiting factor in all applications.

Although coating or juxtaposing common dielectric materials between traditional electrically conductive electrodes and the media under treatment allows higher voltage to be applied, implying a higher E-field intensity, the effect is offset by a much larger voltage drop across the dielectric material being used, thus lowering the E-field in the media under treatment. This occurs because of the manner in which voltage drops, and therefore the E-field, is divided or otherwise distributed in series capacitance networks.

It would be advantageous to develop a system for generating an E-field that significantly mitigates or completely resolves the undesirable effects of the previous systems and methods.

SUMMARY

Accordingly, one embodiment of the present invention includes a high impedance system for generating an electric field and comprises: a pair of electrodes comprising a dielectric material wherein each electrode has at least one surface coated with a conductive material; and wherein such dielectric material forms a barrier separating the conductive coating from the subject fluid under treatment; a fluid pathway or space formed between the pair of electrodes such that the conductive material is on an electrode surface not in contact with the fluid in the pathway or space; a time variant, time invariant, or pulsed voltage source applied across the electrodes; and a housing containing said pair of electrodes, said housing configured to maintain a subject static or dynamic fluid in said pathway or space.

One method embodiment of the present invention includes a method of subjecting a fluid to an electric field comprising: forming a fluid pathway between a pair of electrodes wherein said electrodes comprise a dielectric material and wherein each electrode has at least one surface coated with a conductive material, said conductive material placed on an electrode surface not in the fluid pathway; housing said electrodes such that a subject static or dynamic fluid is maintained in said pathway; applying a time variant, time invariant or pulsed voltage source to each surface of the electrodes coated with the conductive material thereby creating the electric field; and causing a fluid to enter the fluid pathway such that said fluid is subjected to the electric field.

The system and method for generating the E-field utilizes high impedance dielectric materials having a collection of three imperative material properties: high permittivity ($\in$), high volume resistivity ($\rho$) and high maximum allowable E-field stress ($\phi$) and physical geometries that take advantage of the manner in which E-fields are divided or distributed in series capacitance networks.

Other variations, embodiments, and features of the present invention will become evident from the following detailed description, drawings, and claims.

DETAILED DESCRIPTION

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

While embodiments of the present invention have many applications, one embodiment directed to biological cell electroporation is described herein. The term electroporation, sometimes electropermeabilization in patent and academic literature, is widely used to denote phenomena associated with the action of an electric field on the membrane of a living cell. Electroporation of cells suspended in a fluid electrolyte is important in the context of cellular biology, genetic engineering, drug therapy, as well as biotechnology processes such as pasteurization and sterilization. Depending on field intensity, exposure time, and wave-form shapes, impressed electric fields can cause either reversible or irreversible pore formation, as well as other structural defects in lipid membranes, including the membranes of bacteria, fungi, spores, virus, and mammalian (soma) cells. In the case of reversible electroporation, the phenomena is marked by a transient increase in membrane diffusion permeability, which has been used for decades for transfection of DNA, drugs, dyes, proteins, peptides, and other molecules. When the impressed electric field induces a critical transmembrane voltage ($\Phi_c \approx 1$ V for many bacteria types), for a sufficient period, pore formation and other membrane defects become irreversible causing cell death and/or permanent metabolic inactivation, viz. pasteurization or sterilization.

Electroporation devices and methods for clinical and laboratory use have been available for decades, and can be readily purchased for transfection, pasteurization, and sterilization of small batch volumes (typically 1 μl to 100 ml). Much work has been expended over the past two decades to adapt these clinical and laboratory methods to commercial applications that require continuous high flow rates instead of small batch volumes. Many devices and methods have been proposed, implemented, and patented, however, common to all the current and prior art is the use of low impedance electrically conductive electrodes coupled directly to the fluid being treated. This renders the equivalent circuit for such devices to a resistance network in the steady-state mode, accompanied by the parametric requisites of electric conduction current, ohmic heating, interface charge transfer, double layer formation, electrochemical reactions, and excessive energy consumption. These resistive load parametrics account for the ubiquitous use of pulsed waveforms employed in traditional electroporation devices. The use of pulsed wave forms (sometimes termed PEF), whether unipolar, bipolar, or other shapes, and regardless of rise and decay times, are all applied to mitigate the aforementioned undesirable effects of low impedance resistive networks common to current and prior art in this field. In the case of the attempts to adapt these techniques to a commercial pasteurization application, ohmic heating, undesirable electrochemical reactions, and excessive energy consumption have been particularly problematic.

The embodiments of the present invention, coined High Impedance Electroporation by the inventors (hereinafter: HIE), mitigate many of the undesirable effects while proving to be as, or more, effective than prior systems and methods for both batch and high continuous flow rate applications.

Figure 1:
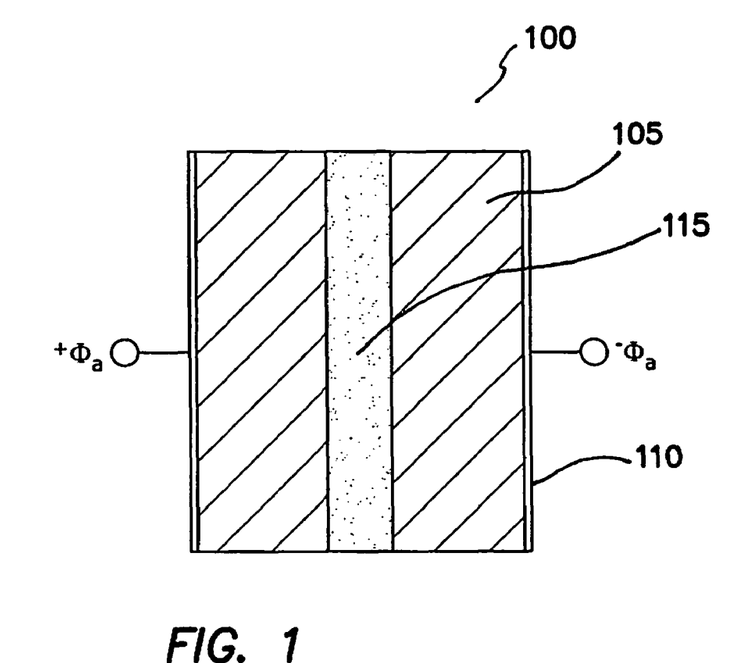
FIG. 1 illustrates a first dielectric configuration of the present invention having a parallel geometry.
Figure 2:
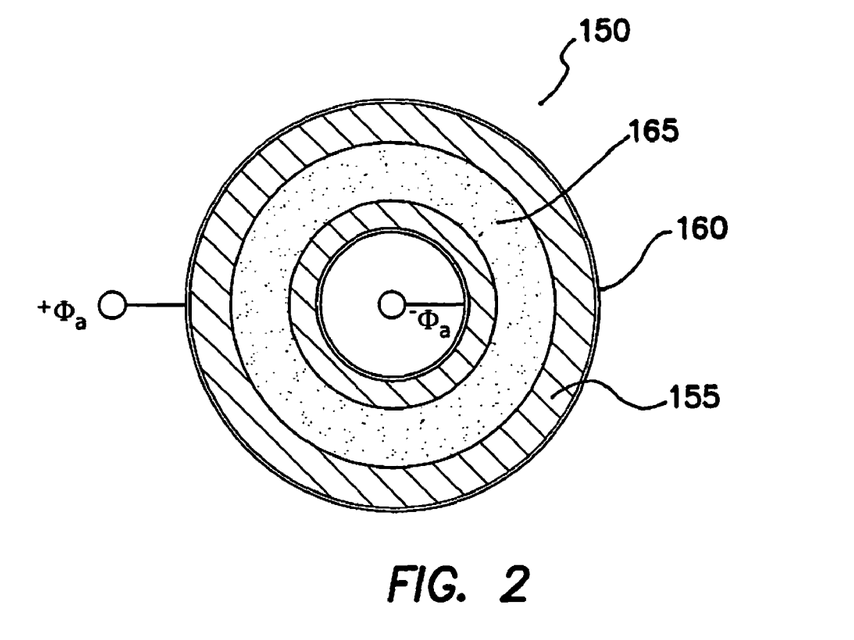
FIG. 2 illustrates a second dielectric configuration of the present invention having a cylindrical geometry.

FIGS. 1 and 2 show a parallel dielectric configuration 100 and a cylindrical dielectric configuration 150, respectively, that may be used to facilitate the method embodiments of the present invention. Each configuration shows a dielectric material 105, 155, electrical conductive coating 110, 160 and material 115, 165 under test or E-field influence.

Figure 3:
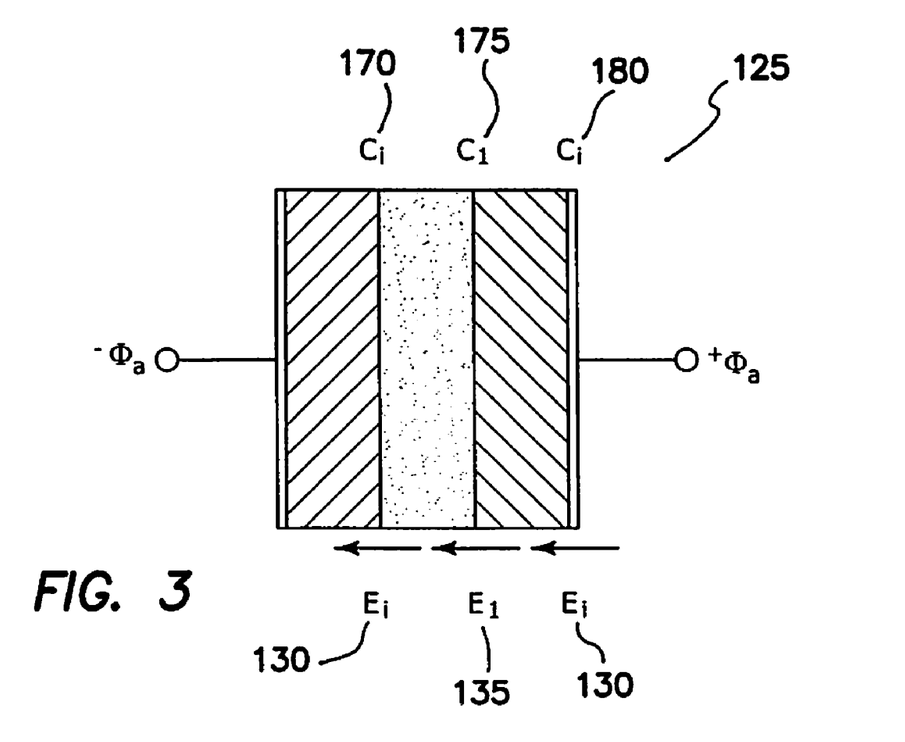
FIG. 3 illustrates three dielectric sections arranged to form a series capacitance network.
Figure 4:
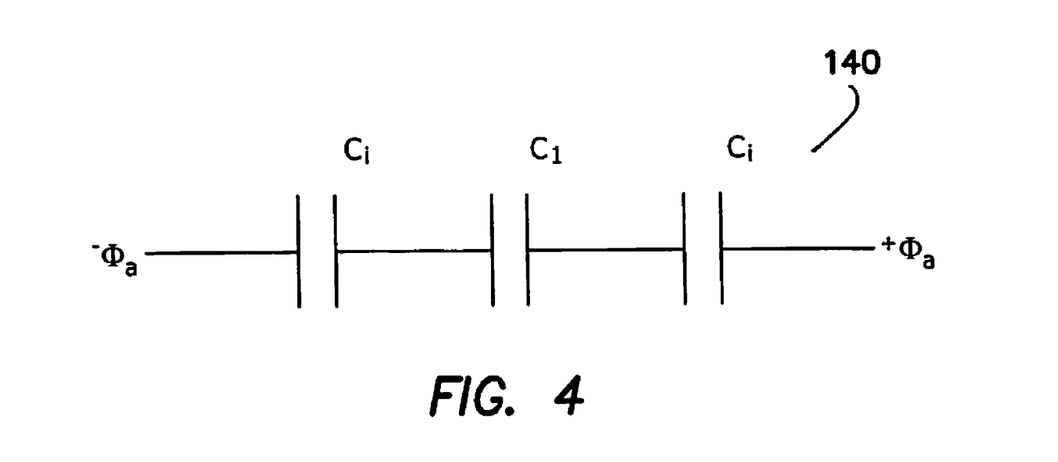
FIG. 4 illustrates a circuit equivalent of the dielectric geometry of FIG. 3.

For capacitive elements forming series networks used to facilitate the embodiments of the present invention, charge displacement is conserved, and the potential gradient (voltage drop), along with the electric field, is distributed proportional to each material's permittivity prior to charge relaxation for each material section in the network. FIG. 3 considers three dielectric sections 170, 175 and 180 arranged to form a series capacitance network 125. E-fields 130, 135 through each are identified. FIG. 4 shows a circuit diagram 140 representing the network 125 of FIG. 3.

Considering the arrangement depicted in FIG. 3, if the permittivity of sections $C_i$ 170 and $C_i$ 180 is significantly greater than $C_1$ 175, during the transient response of a pulse (step function), the potential across, and the E-field through $C_i$ 170 and $C_i$ 180 will be very small compared to the potential across, and the E-field through section $C_1$ 175. This relationship effectively concentrates the total potential gradient available for field development in the center section, ($C_1$ 175 in this example). The same relationship applies to networks comprised of 2, 4, or multiple dielectric section geometries. As a result, a much higher field stress can be impressed through the material under test or treatment than with the methods and devices of current and prior art. Additionally, use of dielectric electrodes with high volume resistivity limit electric current flow, ohmic heating, and energy consumption, as well as preempting undesirable electrochemical reactions at the electrode interfaces.

The inventors hereof demonstrated the effectiveness of the embodiments of the present invention via confidential experimentation. The following description describes the experimentation including the system and methodology utilized. However, those skilled in the art will understand that the scope of the present invention is not limited to the experimental systems and/or methodology utilized.

Figure 5:
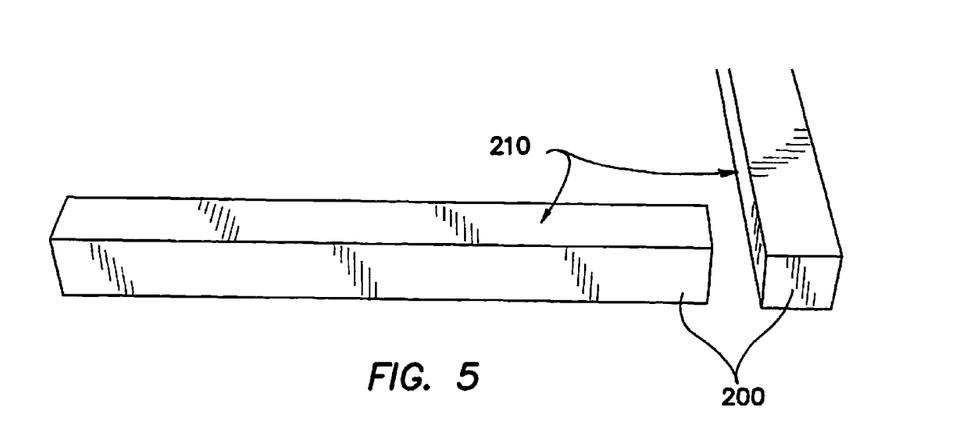
FIG. 5 illustrates two titanate ceramic slabs coated on one side with a thin film of silver metal forming a conductive electrode surface on each.

Now referring to FIG. 5, two high impedance dielectric electrodes 200 fabricated of lead-magnesium-lead titanate ceramic are shown. Other materials, such as a high permittivity particulate/epoxy composite or materials having similar properties can also be used. The two titanate ceramic slabs 200 were coated on one side with a thin film of silver metal forming a conductive surface 210. In one embodiment, the electrodes measured 10 mm thick by 10 mm wide by 100 mm long and the dielectric ceramic had the following electric material properties:

electric permittivity: $5.3e^{-08}$ [$Fm^{-1}$] (relative dielectric constant $\in_r=6,000$);
    volume resistivity: $\approx 10^{12}$ [$\Omega$-cm]; and
    maximum allowable field stress: $9.0e+06$ [$Vm^{-1}$].

Figure 6:
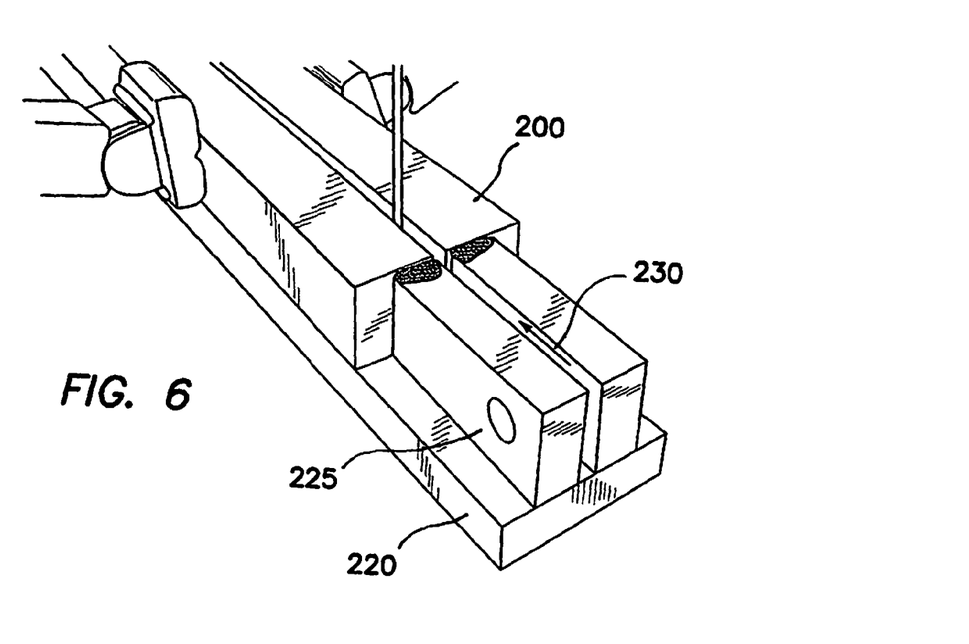
FIG. 6 illustrates a perspective view of the electrodes of FIG. 5 affixed to a polycarbonate beam support with a space between forming a fluid pathway.
Figure 7:
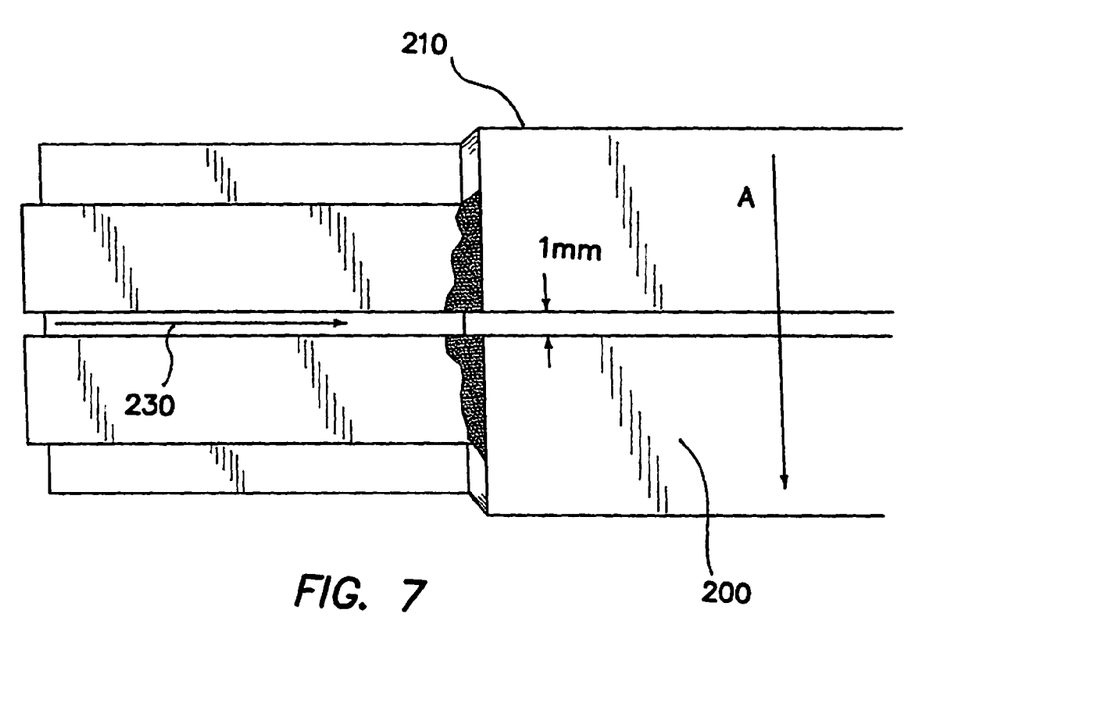
FIG. 7 illustrates a top view of the electrodes of FIG. 6.
Figure 8:
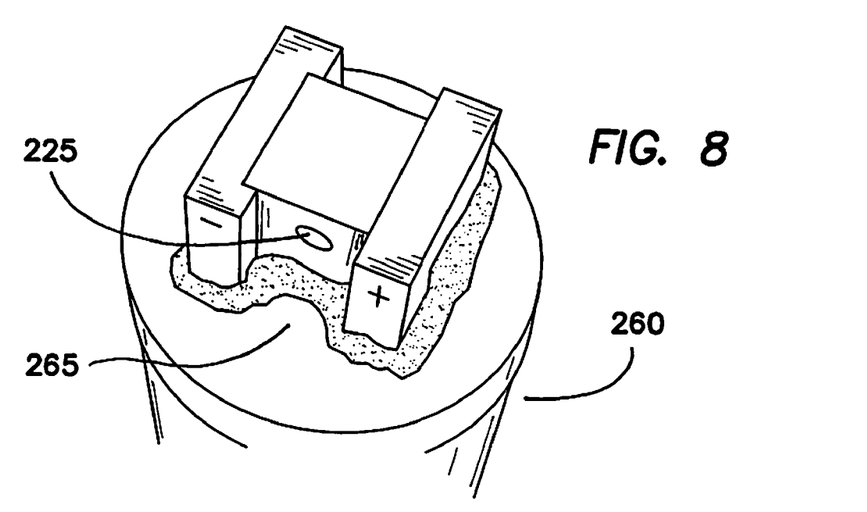
FIG. 8 illustrates an opposing beam support affixed to the other side of the arrangement illustrated in FIGS. 6 and 7.

As shown in FIGS. 6 and 7, the electrodes 200 were affixed to a polycarbonate beam support 220 with a space there between forming a fluid pathway channel 230 measuring 1 mm deep by 10 mm wide by 100 mm long forming a fluid pathway or space volume of 1000 mm$^3$ or 1 ml. A fluid port 225 permits the inflow or outflow of subject fluid. Since the force of attraction imparted by the field between the electrodes 200 is formidable when the system is charged, beam supports 220 were provided as structural strain relief for the ceramic electrodes 200. Note that the electrodes 200 are arranged to form a series capacitance network coupled to the test liquid being treated. Directional arrow A shown in FIG. 7 depicts the direction of the generated E-field. FIG. 8 shows an opposing beam support 250 completing a liquid-tight fluid pathway. Now referring to FIG. 9, the electrodes 200 and beam supports 220 were then fitted into a housing 260 (e.g., a 1¼" PVC pipe), which was filled with a high voltage dielectric epoxy 265. Positive and negative high voltage cable guides 270, 275, respectively, and fluid tube fittings 280, 285 were also affixed to form the final HIE device 300 (termed an abatis by the inventors hereof).

Figure 10:
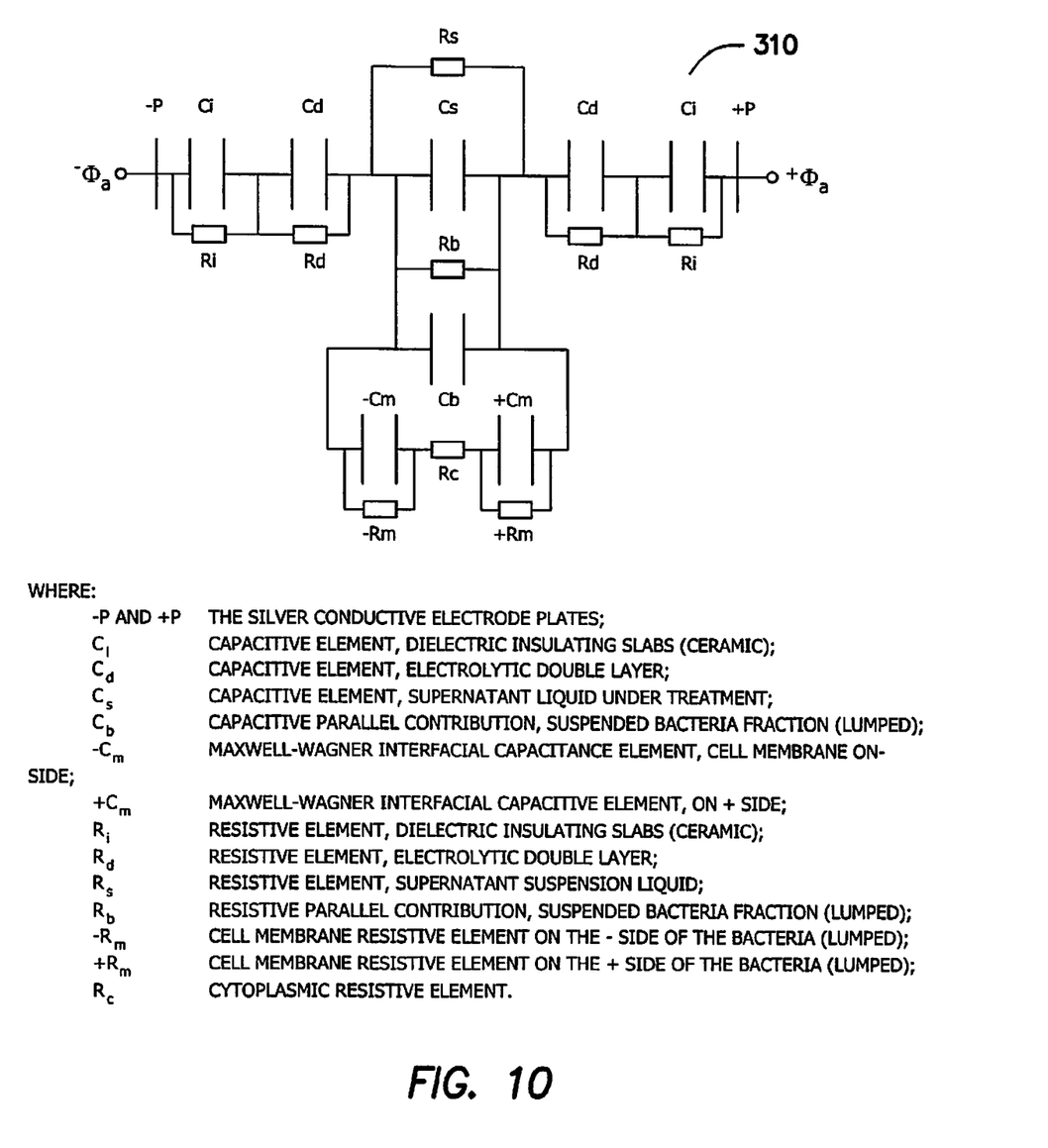
FIG. 10 illustrates an equivalent circuit diagram for the parallel plate geometry of FIGS. 6 and 7.

A liquid/bacteria suspension being treated was passed through the fluid pathway by conveyance tubes connected to the inlet tube fitting 280 and outlet tube fitting 285 as shown. Positive and negative high voltage wires 290, 295, respectively, (shown in FIG. 11) were fed through the positive and negative cable guides 270, 275 and positioned in direct contact with the silver conductive surface 210 of each respective electrode 200 forming an electrical connection for charging the system. FIG. 10 shows an equivalent circuit diagram 310, and legend, for such a parallel plate geometry.

Figure 11:
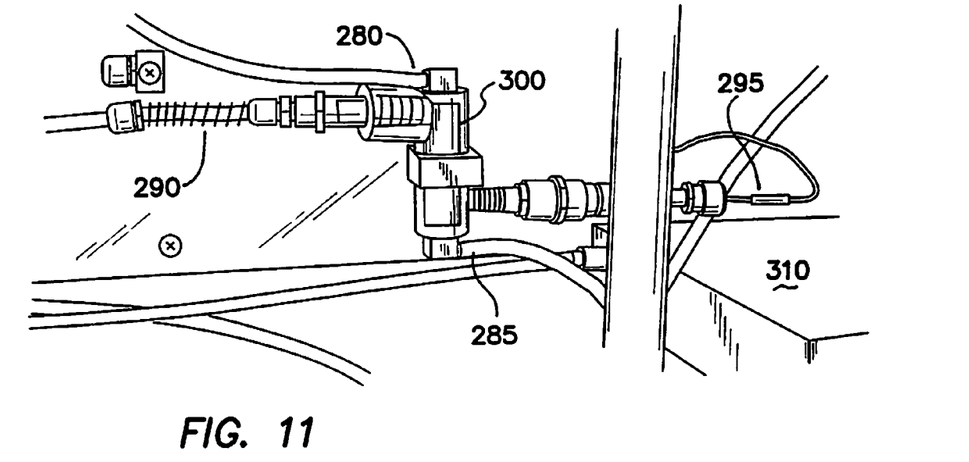
FIGS. 11 and 12 illustrate one exemplary system configuration according to the embodiments of the present invention.
Figure 12:
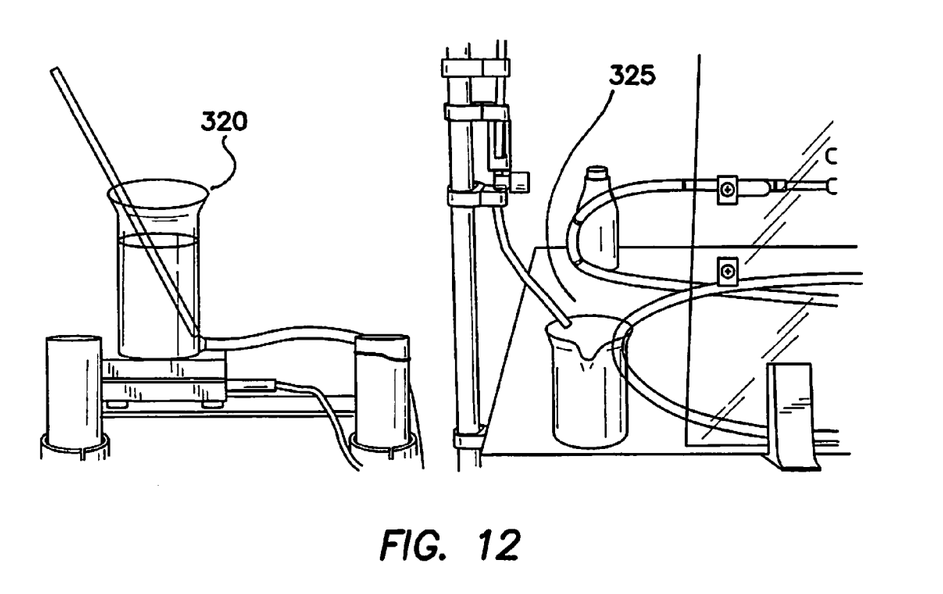
Figure 13:
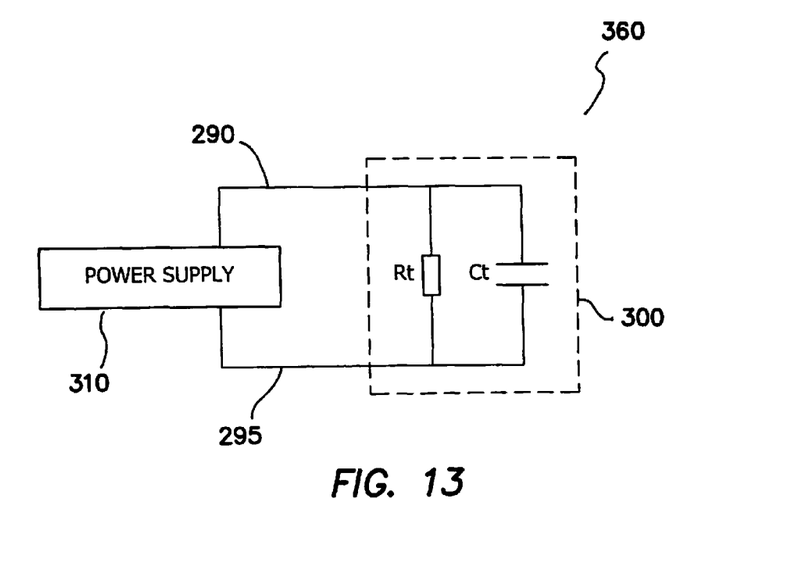
FIG. 13 illustrates an equivalent circuit diagram for the configuration illustrated in FIGS. 11 and 12.

FIGS. 11 and 12 show one complete system configuration 350. For safety reasons, the HIE device 300 was mounted on a high voltage dielectric bulkhead (e.g., ¼" polycarbonate plastic sheet), and wired to a 120 kVDC power supply 310. A first 600 ml fluid supply beaker 320 was mounted vertically above the HIE device 300 such that, by means of gravity, the inoculated liquid would drain to the fluid inlet 280 and through the HIE device 300. A second 600 ml beaker 325 was placed at a level below the HIE device 300 into which treated liquid would drain from the fluid outlet 285. FIG. 13 shows an equivalent circuit diagram 360 for the power supply 310 and HIE device 300.

Figure 9:
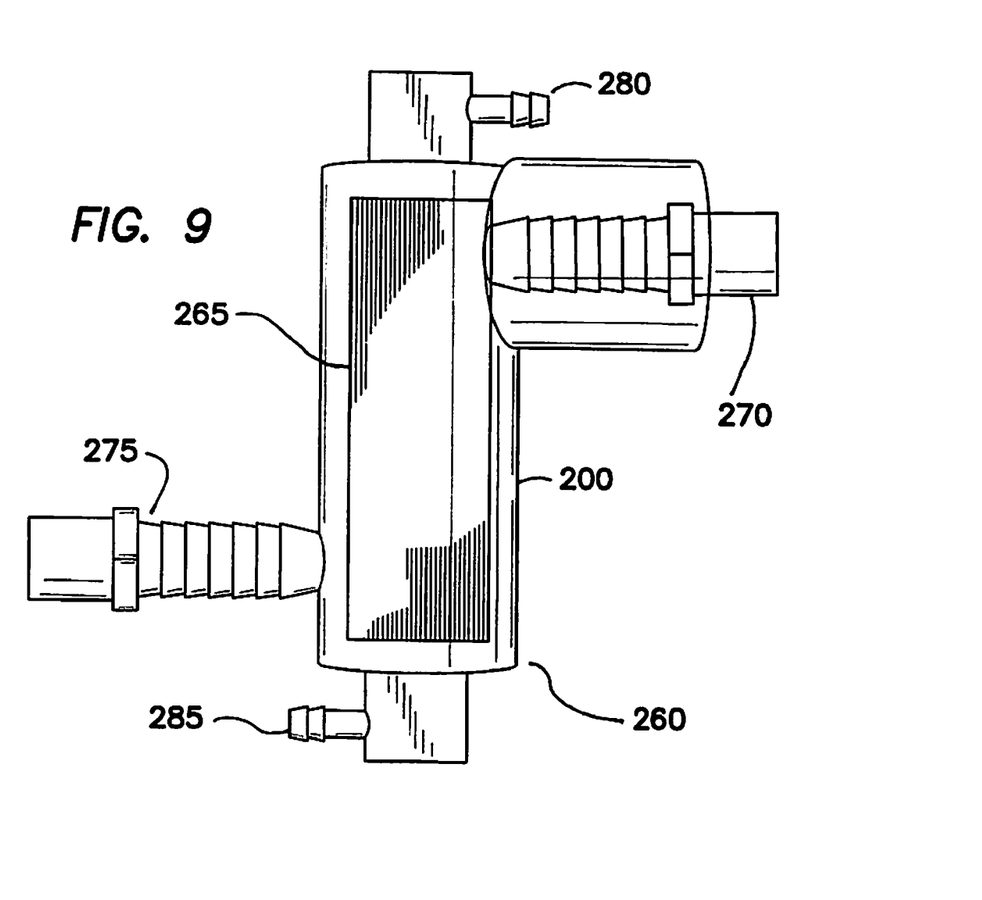
FIG. 9 illustrates one configuration of a high-impedance E-field device of the present invention.

Prior to operating the system with a test liquid inoculated with bacteria, the HIE device 300 was filled with sterile Tryptic Soy Both and its electrical properties were measured. Table #1 shows predicted and measured values:

TABLE #1

|  | $C_t$ [pF] | $R_t$ [$\Omega$] | $E_l$ [$Vm^{-1}$] | $\Phi_a$ [$\Delta V$] | $I_s$ [Å] |
|---|---|---|---|---|---|
| Predicted | 6.00E+02 | 2.50E+11 | 7.82E+07 | 1.00E+05 | 4.00E-07 |
| Measured | 6.52E+02 | 2.20E+11 | 8.50E+07 | 1.00E+05 | 4.55E-07 |

Where:
$C_t$ total effective capacitance, [pF]; Picofarads
$R_t$ total series resistance, [$\Omega$]; ohms
$E_l$ electric field through the liquid under test, [$Vm^{-1}$]; volts per meter
$\Phi_a$ applied voltage (DC), [V]; volts
$I_s$ series current, [Å]; amperes (transient displacement current not measured)

During a 1 μs pulse, the maximum E-field through the liquid under test was on the order of $8.5e+07$ $Vm^{-1}$, which equates to 850 kV/cm, representing a formidable electric field. The electric current through the HIE device 300, however, was on the order of 4.5 e-07 amperes representing an extremely low current given the intense electric field generated (this figure does not include transient displacement current). The measured values represent an average of three (3) separate tests. The power supply was turned off and the HIE device 300 fully discharged between each measurement.

The system 350 for the electroporation test was operated at an applied voltage ($\Phi_a$) of 10 kV. The electric field $E_1$ presented to the inoculated liquid under treatment at this voltage was $7.82e+06$ $Vm^{-1}$ or about 78 kV/cm. On the physical scale of *E. coil* bacteria, this field equates to 7.82 V$\mu m^{-1}$ and is sufficient to achieve the critical transmembrane potential (e.g., $\Phi_c \approx 1$ volt) often cited as a threshold for membrane electroporation. Electric conduction current ($I_a$) through the HIE device 300 during the test was approximately 4.6 e-08 Å (0.046 microamperes). Average power consumption $P_{avg}$ at the HIE device 300 only, not including cable and power supply losses, was on the order of 4.6 e-04 W (460 microwatts). Since the volume of the treated liquid was 600 ml, and the total time for complete flow-through was approximately 480 seconds, the total energy dissipation $U_t$ was on the order of 2.2 e-01 J (221 millijoules), putting the specific energy consumption $U_s$ at 1.75 e-03 kJ/1$R_{log}$ (1.75 joules/liter-log reduction).

The cumulative exposure time ($t_s$) was ~800 ms, an average, against flow rate over the 480 second total process time. The bacterial load in the test liquid was reduced by 38% (kill fraction in terms of cfu/ml), or a log reduction of approximately −0.21 $\log_{10}$. The kill fraction stated is an average of seven intercepted samples taken at equal intervals during the test period. Although a −0.21 log reduction is not significant for the purpose of commercial pasteurization, it is significant for the purpose of demonstrating the effectiveness of the embodiments of the present invention as applied to live cell electroporation. No attempt was made to detect or measure the extent of reversible electroporation (i.e. a transient increase in membrane permeability), but given the large kill fraction, electropermeabilization effects in the cohabitant survival fraction are immutable.

A survey of commercial, academic, and patent literature covering the scope of electroporation devices, methods, and theory uncovered various applied voltages, field intensities, waveforms, pulse rates, rise/decay profiles, geometries, and fluid flow schemes. All of the current and prior art employ low impedance electrically conductive electrodes coupled directly to the liquid under treatment, thus rendering the equivalent circuit a predominately resistive load in the steady-state condition (there are elements of capacitance and inductance in all resistance networks, however, these circuit elements are not pertinent to this exam). Such is true for clinical, laboratory and commercial systems. However, the embodiments of the present invention comprise a series capacitance network. The following table presents an overview of critical electrical parameters for the operating electroporation devices and systems surveyed (the range of some values is broad, but still instructive):

TABLE #2

|  | $\Phi_a$ | $E_1$ | | $t_p$ | $f_p$ | $U_s$ |
|---|---|---|---|---|---|---|
|  | [kV] | [Vm$^{-1}$] | [kVcm$^{-1}$] | [μs] | [Hz] | [kJ/lR$_{log}$] |
| Minimum Value Reported | <0.1 | 5.00E+02 | 0.005 | 0.001 | 100 | 25 |
| Maximum Value Reported | 75 | 8.70E+06 | 87 | 300 | 1.00E+06 | 11,300 |

Where:
$\Phi_a$ applied voltage, [kV]; kilovolts
$E_1$ field intensity, [Vm$^{-1}$] and [kVcm$^{-1}$]; volts per meter, & kilovolts per centimeter
$t_p$ pulse width, [μs]; microseconds
$f_p$ pulse frequency, [Hz]; hertz (as pulses per second, not cycles per second)
$U_s$ specific energy, [kJ/lR$_{log}$]; kilojoules per liter per log reduction The data collected from the study encompass a wide range of both reversible (transient permeabilization) and irreversible (death) electroporation effects, a number of different bacteria types, and includes systems with coaxial (cylindrical) and parallel fluid pathway geometries, as well as both batch type and continuous flow schemes. However, the specific energy $U_s$ required by the device or method to affect the kill fraction attained was seldom cited (last column in Table #2). The survey conducted by the inventors, often requiring calculations extramural to the reports under study, revealed the magnitude of energy consumption versus kill fraction to be quite high as shown. By contrast, the HIE electroporation device 300 fabricated for the instant demonstration expended a specific energy ($U_s$) on the order of 1.75 e-03 kJ/1R$_{log}$, some 4 orders of magnitude lower than the lowest specific energy ($U_s$) reported, and 6 orders of magnitude less than the highest specific energy ($U_s$) reported. This low energy consumption per liter per log reduction, owing to the high impedance of the embodiments of the present invention, is in addition to completely resolving the problems of fluid/electrode electrochemistry and ohmic heating presented by the current and prior art in this field.

Those skilled in the art will recognize that even though a time invariant DC voltage (square-wave pulse) was used to charge (energize) the HIE device 300 in the instant demonstration, a time variant (AC) applied voltage can also be used. In addition, while a parallel plate geometry was employed for series capacitance geometry, other geometries, such as coaxial (cylindrical series capacitance), are equally applicable.

Further to the application of high impedance field generation to the electroporation of biological cells, the inventors have found a concordant action between the application of acoustic energy and electroporation. The acoustic energy can be applied via any desired means. For example, the acoustic energy can be applied 1) by action of a piezoelectric transducer attached to the HIE device 300 in such a manner and in such a configuration as to impart the acoustic energy to the fluid in the pathway 230 or space concurrent with, concatenated between, and/or consequent to the applied electric field pulse or pulses; or, 2) by action of a piezoelectric response of the dielectric electrode 200 itself wherein the material chosen as the barrier material has suitable dielectric properties and is also a piezoelectric material. In such a case, the acoustic energy is imparted to the fluid under treatment or test concurrently (in both space and time) with the application of the applied potential. In this case, the acoustic energy has the same pulse duration time and pulse interval as the applied field. It is also possible that both means of applying the acoustic energy can be employed n a single system. That is, the dielectric electrode formed of a piezoelectric material acts to impart the electric field and the acoustic energy to the fluid under treatment simultaneously, while a second dedicated electroacoustic or mechanoacoustic transducer is positioned and configured to impart acoustic energy to the fluid under treatment either concurrently with, concatenated between, and/or consequent to the applied field.

The application of a pulsed acoustic longitudinal wave front to a biological cell during or immediately after being electroporated presents a periodic radiation pressure to the cell membrane. Since electroporation causes open pores to develop through the cellular membrane, the action of the radiation pressure, presented as a force perpendicular to the polar axis of the cell membrane, causes the cell to deform. Given the mass inertia of the cell and the viscosity of the supernatant, the cell flattens at the pole under the influence of the radiation force. As the cell membrane flattens at the pole (the polar axis being parallel to the radiation force vector), the incident angle between the radiation vector and portions of the membrane radial to the polar axis progressively decrease, that is, become more perpendicular to the force vector, thus advancing the flattening process. This process of flattening continues until the radiation force is overcome by the counter inertial and viscous forces at play and the cell begins to move. During the flattening period, however, either, or both, of two things occur relative to the cell's geometry: 1) the cell's internal volume decreases or 2) the membrane area increases (by stretching). The force resulting from the normal plan-wave longitudinal acoustic radiation pressure is a steady state phenomenon, hence the flattening action only occurs once, after which, the cell's shape tends to recover, and then the entire cell tends to move with the wave front. If the acoustic energy is pulsed however, the flattening/recovery action proceeds at the pulse rate, provided the pulse rate is presented at a lower frequency than the mechanical shape recovery relaxation time of the cell. Because the deformation periodically increases and decreases the internal volume of the cell, the result is a "pumping" action. The pumping action causes cytoplasmic fluid to be pumped out of the cell, as well as extra-cellular fluid (supernatant) to be pumped into the cell. The action serves to hasten or accelerate cellular paralysis leading to death and/or metabolic inactivation of the organism thus improving the efficiency and/or kill fraction for a given electric field intensity and field exposure period.

Although the present invention has been described in detail with reference to several embodiments, additional variations and modifications exist within the scope and spirit of the present invention as described and defined in the following claims.

We claim:

1. A high impedance system for generating an electric field comprising:
   a pair of electrodes comprising a dielectric material wherein each electrode has at least one surface coated with an electrically conductive material, and wherein said dielectric material forms a barrier separating the conductive coating from the subject fluid under treatment, said dielectric material having a combination of permittivity, maximum allowable electric field stress and volume resistivity for substantially forestalling electric conduction current through said subject fluid while simultaneously directing and generating said electric field through said subject fluid with sufficient field intensity and duration causing reversible and/or irreversible electroporation in biologic cells suspended in said subject fluid;
   a fluid pathway or space area formed between the pair of electrodes such that the conductive material is on an electrode surface not in contact with the subject fluid in the pathway or space;
   a time variant, time invariant, or pulsed voltage source applied across the electrodes; and
   a housing containing said pair of electrodes, said housing configured to maintain a subject static or dynamic fluid in said pathway or space.

2. The system of claim 1 wherein the dielectric material has collectively a static permittivity greater than 8.8E-11 $Fm^{-1}$@<1.0 KHz, a volume resistivity greater than 1.0E+04 $\Omega cm$, and a maximum allowable electric field stress greater than 1.0 $kVmm^{-1}$.

3. The system of claim 1 wherein the electrodes are elongated, square in cross-section, and arranged in parallel.

4. The system of claim 3 wherein the fluid pathway or space is between the electrodes.

5. The system of claim 1 wherein the electrodes are elongated tubes having different diameters.

6. The system of claim 5 wherein the electrodes are arranged in a coaxial geometry with the smaller diameter electrode positioned within the larger diameter electrode forming an annular fluid pathway or space there between.

7. The system of claim 6 wherein an outer surface of the larger diameter electrode and an inner surface of the smaller diameter electrode is coated with an electrically conductive material.

8. The system of claim 1 wherein the dielectric barrier material is high permittivity ceramic or particulate/epoxy composite.

9. The system of claim 1 wherein a fluid under test or treatment is in liquid, gas, or solid phase.

10. The system of claim 1 further comprising means for applying pulsed acoustic energy to the subject fluid.

11. The system of claim 1 further comprising an electroacoustic or mechanoacoustic transducer operable to apply acoustic energy to the subject fluid.

12. The system of claim 1 wherein the electrodes are fabricated of a piezoelectric material operable to apply acoustic energy to the subject fluid.

13. The system of claim 1 further comprising an electroacoustic or mechanoacoustic transducer operable to apply acoustic energy to the subject fluid.

14. The system of claim 1 wherein the electrodes are fabricated of a piezoelectric material operable to apply acoustic energy to the subject fluid.

15. A high impedance system for generating an electric field comprising:
   a pair of electrodes comprising a dielectric material wherein each electrode has at least one surface coated with an electrically conductive material, said dielectric material forming a barrier separating the conductive coating from the subject fluid under test or treatment, and having a permittivity of greater than 8.8E-11 $Fm^{-1}$@<1.0 KHz, a volume resistivity greater than 1.0E+04 $\Omega cm$ and a maximum allowable electric field stress greater than 1.0 $kVmm^{-1}$ whereby said dielectric material substantially forestalls electric conduction current through said subject fluid while simultaneously directing and generating said electric field through said subject fluid with sufficient field intensity and duration causing reversible and/or irreversible electroporation in biologic cells suspended in said subject fluid;
   a fluid pathway or space formed between the pair of electrodes such that the conductive material is on an electrode surface not in contact with the subject fluid in the pathway or space;
   a time variant, time invariant, or pulsed voltage source applied across the electrodes wherein the dielectric material is arranged in a parallel or coaxial geometry forming a series capacitance network with the fluid under test or treatment concentrating or intensifying the electric field presented to said fluid; and
   a housing containing said pair of electrodes, said housing configured to maintain a subject static or dynamic fluid in said pathway or space.

16. The system of claim 15 wherein the dielectric barrier material insulates the fluid from the electrically conductive coating substantially preventing faradaic current and electrochemistry at the fluid/electrode interfaces.

17. The system of claim 15 wherein the dielectric barrier material further insulates the fluid from the electrically conductive coating substantially preventing electronic and ionic conduction current through, and ohmic heating of, the system.

18. The system of claim 15 further comprising a device for applying pulsed acoustic energy to the subject fluid under electric field treatment or test, said acoustic energy being applied concurrent in time or space, and/or concatenated in time or space, and/or consequent in time or space to/with the application of the electric field.

19. A high impedance system for generating an electric field comprising:
- a pair of electrodes comprising a dielectric material wherein each electrode has at least one surface coated with an electrically conductive material, and wherein said dielectric material forms a barrier separating the conductive coating from the subject fluid under treatment;
- a fluid pathway or space area formed between the pair of electrodes such that the conductive material is on an electrode surface not in contact with the subject fluid in the pathway or space;
- a time variant, time invariant, or pulsed voltage source applied across the electrodes;
- a housing containing said pair of electrodes, said housing configured to maintain a subject static or dynamic fluid in said pathway or space; and
- means for applying pulsed acoustic energy to the subject fluid.

20. The system of claim 19 wherein said means for applying pulsed acoustic energy to said subject fluid comprises an electroacoustic or mechanoacoustic transducer.

21. The system of claim 19 wherein said means for applying pulsed acoustic energy to said subject fluid comprises electrodes fabricated of a piezoelectric material.

22. A high impedance system for generating an electric field comprising:
- a pair of electrodes comprising a dielectric material wherein each electrode has at least one surface coated with an electrically conductive material, said dielectric material forming a barrier separating the conductive coating from the subject fluid under test or treatment, and having a permittivity of greater than 8.8E-11 $Fm^{-1}$@<1.0 KHz, a volume resistivity greater than 1.0E+04 $\Omega$cm and a maximum allowable electric field stress greater than 1.0 $kVmm^{-1}$;
- a fluid pathway or space formed between the pair of electrodes such that the conductive material is on an electrode surface not in contact with the subject fluid in the pathway or space;
- a time variant, time invariant, or pulsed voltage source applied across the electrodes wherein the dielectric material is arranged in a parallel or coaxial geometry forming a series capacitance network with the fluid under test or treatment concentrating or intensifying the electric field presented to said fluid;
- a housing containing said pair of electrodes, said housing configured to maintain a subject static or dynamic fluid in said pathway or space; and
- a device for applying pulsed acoustic energy to the subject fluid.

23. The system of claim 22 wherein said device for applying pulsed acoustic energy to said subject fluid comprises an electroacoustic or mechanoacoustic transducer.

24. The system of claim 22 wherein said device for applying pulsed acoustic energy to said subject fluid comprises electrodes fabricated of a piezoelectric material.

* * * * *